US012248045B2

United States Patent
Bharkhada et al.

(10) Patent No.: US 12,248,045 B2
(45) Date of Patent: Mar. 11, 2025

(54) COLLOCATED PET AND MRI ATTENUATION MAP ESTIMATION FOR RF COILS ATTENUATION CORRECTION VIA MACHINE LEARNING

(71) Applicant: Siemens Medical Solutions USA, Inc., Malvern, PA (US)

(72) Inventors: Deepak Bharkhada, Knoxville, TN (US); Vladimir Panin, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 332 days.

(21) Appl. No.: 17/031,974

(22) Filed: Sep. 25, 2020

(65) Prior Publication Data

US 2022/0099770 A1   Mar. 31, 2022

(51) Int. Cl.
*G01R 33/48* (2006.01)
*A61B 5/055* (2006.01)
*A61B 6/00* (2024.01)
*G01R 33/56* (2006.01)
*G06T 7/00* (2017.01)

(52) U.S. Cl.
CPC ............ *G01R 33/481* (2013.01); *A61B 5/055* (2013.01); *A61B 6/5247* (2013.01); *G01R 33/5608* (2013.01); *G06T 7/0012* (2013.01); *G06T 2207/10104* (2013.01); *G06T 2207/20081* (2013.01)

(58) Field of Classification Search
CPC ........ G01R 33/50; G01R 33/561; A61B 5/055
See application file for complete search history.

(56) References Cited

U.S. PATENT DOCUMENTS 9,474,495 B2 * 10/2016 Ahn ................. A61B 6/032
2021/0012543 A1 * 1/2021 Hein ................. G06T 11/008

FOREIGN PATENT DOCUMENTS

WO   2010/018478   2/2010
WO   2010/097714   9/2010

OTHER PUBLICATIONS

Donghwi Hwang, Improving the Accuracy of Simultaneously Reconstructed Activity and Attenuation Maps Using Deep Learning, The Journal of Nuclear Medicine (Year: 2018).*
Maike E. Lindemann, Impact of improved attenuation correction on 18F-FDG PET/MR hybrid imaging of the heart, PLOS ONE (Year: 2019).*
Heußer, Thorsten, et al., "MLAA-based attenuation correction of flexible hardware components in hybrid PET/MR imaging," EJNMMI Physics, (2017) 4:12, DOI 10.1186/s40658-017-0177-4.

* cited by examiner

Primary Examiner — Serkan Akar

(57) ABSTRACT

Various systems and computer-implemented methods for Radio Frequency (RF) coil attenuation correction are disclosed. PET time-of-flight (TOF) data generated by a PET imaging modality collocated with an MR imaging modality is received. RF coil attenuation data is extracted from the PET TOF data and an initial RF coil attenuation map is generated. A trained model configured to improve a signal to noise ratio of the initial RF coil attenuation map is applied to generate a final RF coil attenuation map. Attenuation correction of the PET TOF data is performed based on the final RF coil attenuation map. An image is reconstructed from attenuation corrected PET TOF data.

19 Claims, 6 Drawing Sheets

US 12,248,045 B2

COLLOCATED PET AND MRI ATTENUATION MAP ESTIMATION FOR RF COILS ATTENUATION CORRECTION VIA MACHINE LEARNING

TECHNICAL FIELD

This application relates generally to attenuation correction of nuclear imaging and, more particularly, to attenuation correction of nuclear imaging using radiofrequency coils.

BACKGROUND

During nuclear imaging, a patient is positioned on a table and data is obtained using one or more scanning modalities, such as, for example, computerized-tomography (CT), positron-emission tomography (PET), single-photon emission computerized tomography (SPECT), magnetic resonance (MR) etc. Multiple data sets can be collected for a single patient. Different types of reconstructions are generated to control for and/or eliminate artifacts. Although each reconstruction uses different parameters, the underlying patient is the same for each reconstruction.

In PET/MR scans, attenuation correction is performed to provide quantitatively accurate radio-isotope distributions from various imaging modalities. For example, CT scans can be conducted or Dixon Sequence in MR can be utilized to obtain attenuation map information, which is used to perform attenuation correction. However, current attenuation correction fails to account for attenuation caused by body coils during data acquisition.

SUMMARY

In various embodiments, a computer-implemented method for attenuation correction is disclosed. PET time-of-flight (TOF) data generated by a PET imaging modality collocated with an MR imaging modality is received. An initial RF coil attenuation map is generated. A trained model configured to improve a signal to noise ratio of the initial RF coil attenuation map is applied to generate a final RF coil attenuation map. Attenuation correction of the PET TOF data is performed in part based on the final RF coil attenuation map. An image is reconstructed from attenuation corrected PET TOF data.

In various embodiments, a system including a PET TOF imaging modality, an MR imaging modality including a plurality of radiofrequency (RF) coils, a non-transitory memory having instructions stored thereon, and a processor configured to read the instructions is disclosed. The processor is configured to receive PET TOF data, generate an initial RF coil attenuation map, apply a trained model configured to improve a signal to noise ratio of the initial RF coil attenuation map to generate a final RF coil attenuation map, perform attenuation correction of the PET TOF data based on the final RF coil attenuation map, and reconstruct an image from attenuation corrected first set of scan data.

In various embodiments, a computer-implemented method of training a model for generating an RF-coil attenuation map is disclosed. A set of training data including PET TOF data and one or more ground truth attenuation maps is received. Each of the one or more attenuation maps is associated with a subset of the PET TOF data. An untrained model is iteratively trained based on the set of training data and a trained model configured to increase a signal to noise ratio of an initial RF coil attenuation map to generate a final RF coil attenuation map is output.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description.

In the following, various embodiments are described with respect to the claimed providing systems as well as with respect to the claimed methods. Features, advantages or alternative embodiments herein can be assigned to the other claimed objects and vice versa. In other words, claims for the providing systems can be improved with features described or claimed in the context of the methods. In this case, the functional features of the method are embodied by objective units of the providing system.

Furthermore, in the following, various embodiments are described with respect to methods and systems for performing attenuation correction including RF coil attenuation correction as well as with respect to methods and systems for training a neural network to generate an RF coil attenuation map. Features, advantages or alternative embodiments herein can be assigned to the other claimed objects and vice versa. In other words, claims for methods and systems for training a neural network to generate an RF coil attenuation map can be improved with features described or claimed in context of the methods and systems for performing attenuation correction including RF coil attenuation correction, and vice versa.

In general, a trained function mimics cognitive functions that humans associate with other human minds. In particular, by training based on training data the trained function is able to adapt to new circumstances and to detect and extrapolate patterns.

In general, parameters of a trained function can be adapted by means of training. In particular, a combination of supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Qlearning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

Figure 1:
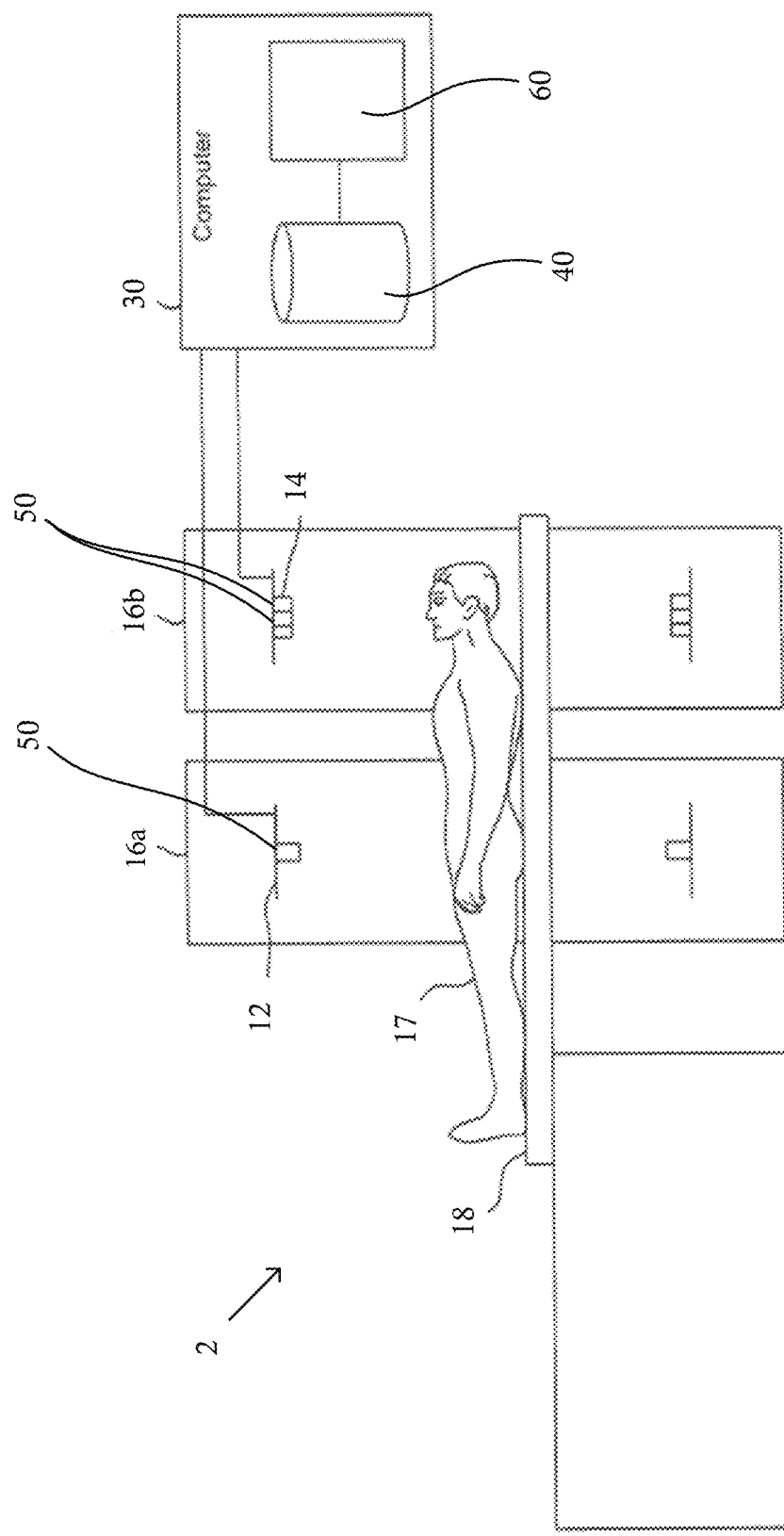
FIG. 1 illustrates a nuclear imaging system, in accordance with some embodiments.

FIG. 1 illustrates one embodiment of a nuclear imaging system 2, in accordance with some embodiments. The nuclear imaging system 2 includes a scanner for at least a first modality 12 provided in a first gantry 16a. The first modality 12 can include any suitable imaging modality, such as a positron emission tomography (PET) modality, a single-photon emission computerized tomography (SPECT) modality, etc. A patient 17 lies on a movable patient bed 18 that can be movable between a gantry. In some embodiments, the nuclear imaging system 2 includes a scanner for a second imaging modality 14, which can be collocated with the first imaging modality and/or provided in a second gantry 16b. The second imaging modality 14 can be any suitable imaging modality, such as, for example, a magnetic resonance (MR) imaging modality or any other suitable imaging modality. Each of the first imaging modality 12 and/or the second imaging modality 14 can include one or more detectors 50 configured to detect an annihilation photon, gamma ray, and/or other nuclear imaging event. In some embodiments, the detectors 50 of the second imaging modality 14 includes a plurality of radiofrequency (RF) coils.

Scan data from the first modality 12 and/or the second modality 14 is stored at one or more computer databases 40 and processed by one or more computer processors 60 of a computer system 30. The graphical depiction of computer system 30 in FIG. 1 is provided by way of illustration only, and computer system 30 can include one or more separate computing devices. The nuclear imaging data sets can be provided by the first modality 12, the second modality 14, and/or can be provided as a separate data set, such as, for example, from a memory coupled to the computer system 30. The computer system 30 can include one or more processing electronics for processing a signal received from one of the plurality of detectors 50. In some embodiments, the computer system 30 is configured to store body coil (or RF coil) data for each detector 50.

In some embodiments, the computer system 30 is configured to generate one or more reconstructions based on the nuclear imaging data obtained by the first modality 12 and/or the second modality 14. Each reconstruction can be generated using any suitable reconstruction parameters, such as any suitable reconstruction algorithms, noise values, event counts, etc. The reconstruction(s) can be generated based on attenuation-corrected scan data. Attenuation correction can be performed based on one or more attenuation maps, such as a RF coil attenuation map, a CT attenuation map, and/or from MR using Dixon sequence, as discussed in greater detail below.

Figure 2:
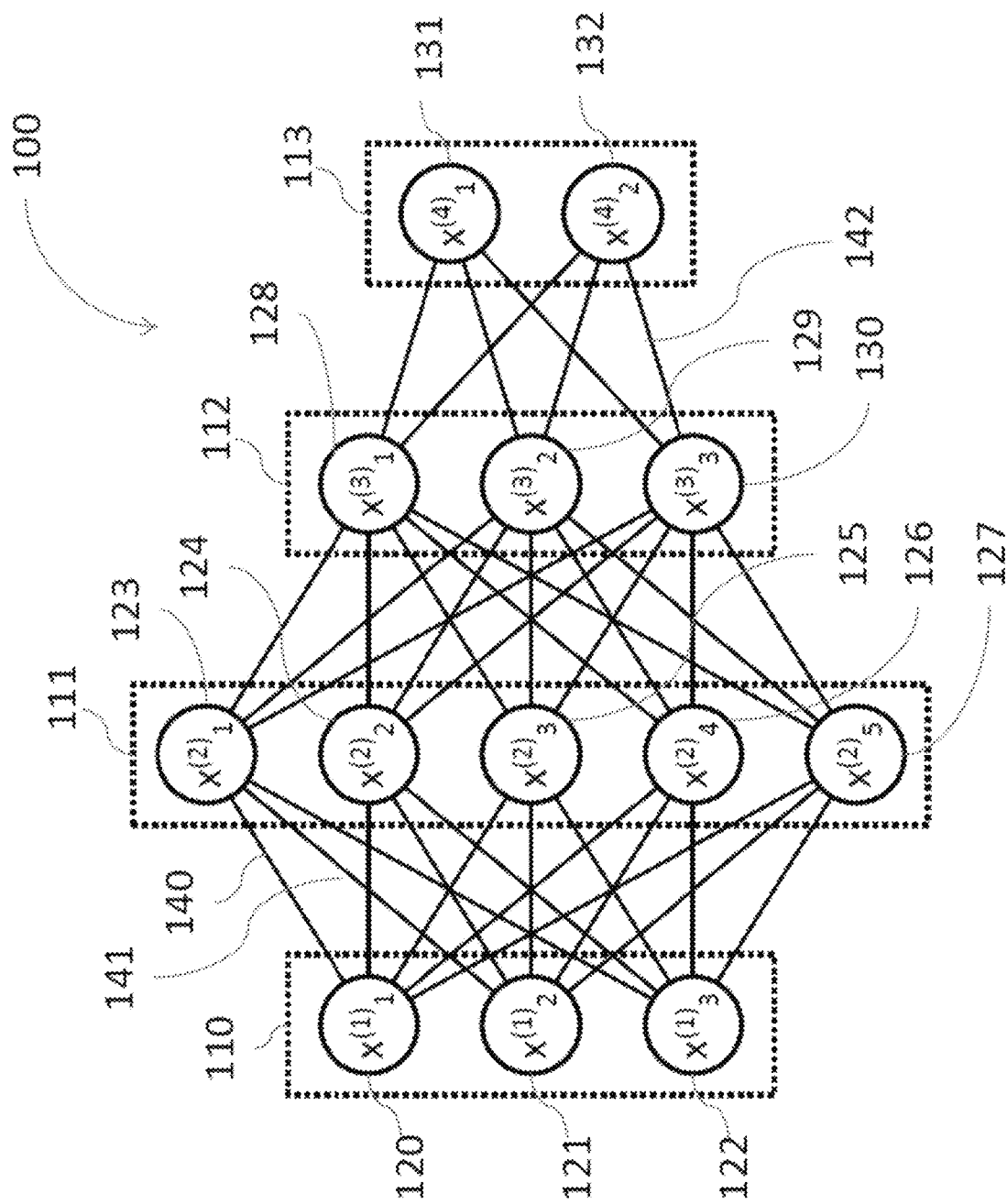
FIG. 2 illustrates an embodiment of an artificial neural network, in accordance with some embodiments.

FIG. 2 displays an embodiment of an artificial neural network 100. Alternative terms for "artificial neural network" are "neural network," "artificial neural net," "neural net," or "trained function." The artificial neural network 100 comprises nodes 120-132 and edges 140-142, wherein each edge 140-142 is a directed connection from a first node 120-132 to a second node 120-132. In general, the first node 120-132 and the second node 120-132 are different nodes 120-132, although it is also possible that the first node 120-132 and the second node 120-132 are identical. For example, in FIG. 2 the edge 140 is a directed connection from the node 120 to the node 123, and the edge 142 is a directed connection from the node 130 to the node 132. An edge 140-142 from a first node 120-132 to a second node 120-132 is also denoted as "ingoing edge" for the second node 120-132 and as "outgoing edge" for the first node 120-132.

In this embodiment, the nodes 120-132 of the artificial neural network 100 can be arranged in layers 110-113, wherein the layers can comprise an intrinsic order introduced by the edges 140-142 between the nodes 120-132. In particular, edges 140-142 can exist only between neighboring layers of nodes. In the displayed embodiment, there is an input layer 110 comprising only nodes 120-122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120-122 within the input layer 110 usually relates to the number of input values of the neural network, and the number of nodes 131, 132 within the output layer 113 usually relates to the number of output values of the neural network.

In particular, a (real) number can be assigned as a value to every node 120-132 of the neural network 100. Here, $x^{(n)}_i$ denotes the value of the i-th node 120-132 of the n-th layer 110-113. The values of the nodes 120-122 of the input layer 110 are equivalent to the input values of the neural network 100, the values of the nodes 131, 132 of the output layer 113 are equivalent to the output value of the neural network 100. Furthermore, each edge 140-142 can comprise a weight being a real number, in particular, the weight is a real number within the interval [−1, 1] or within the interval [0, 1]. Here, $w^{(m,n)}_{i,j}$ denotes the weight of the edge between the i-th node 120-132 of the m-th layer 110-113 and the j-th node 120-132 of the n-th layer 110-113. Furthermore, the abbreviation $w^{(n)}_{i,j}$ is defined for the weight $w^{(n,n+1)}_{i,j}$.

In particular, to calculate the output values of the neural network 100, the input values are propagated through the neural network. In particular, the values of the nodes 120-132 of the (n+1)-th layer 110-113 can be calculated based on the values of the nodes 120-132 of the n-th layer 110-113 by $$x_j^{(n+1)} = f(\Sigma_i x_i^{(n)} \cdot w_{i,j}^{(n)})$$

Herein, the function f is a transfer function (another term is "activation function"). Known transfer functions are step functions, sigmoid function (e.g. the logistic function, the generalized logistic function, the hyperbolic tangent, the Arctangent function, the error function, the smooth step function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values $w^{(m,n)}_{i,j}$ for the edges, the neural network 100 has to be trained using training data. In particular, training data comprises training input data and training output data (denoted as $t_i$). For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 113, wherein f' is the first derivative of the activation function, and $y^{(n+1)}_j$ is the comparison training value for the j-th node of the output layer 113.

In some embodiments, the neural network 100 is configured, or trained, to generate or revise an RF coil attenuation map. For example, in some embodiments, the neural network 100 is configured to receive PET TOF data obtained by one or more detectors 50 during a scan of a first patient. The PET TOF data includes attenuation caused by collocated RF coils of the second imaging modality 14. The neural network 100 can receive the PET TOF data in any suitable form, such as, for example, a listmode or sinogram data, raw data, etc. The neural network 100 is trained to generate an RF coil attenuation map (e.g., mu-map) based on the PET TOF data, for example, by using an MLAA algorithm to extract RF coil attenuation information and applying one or more processes for improving a signal to noise (SNR) ratio of an RF coil attenuation map generated from the extracted RF coil attenuation information.

Figure 3:
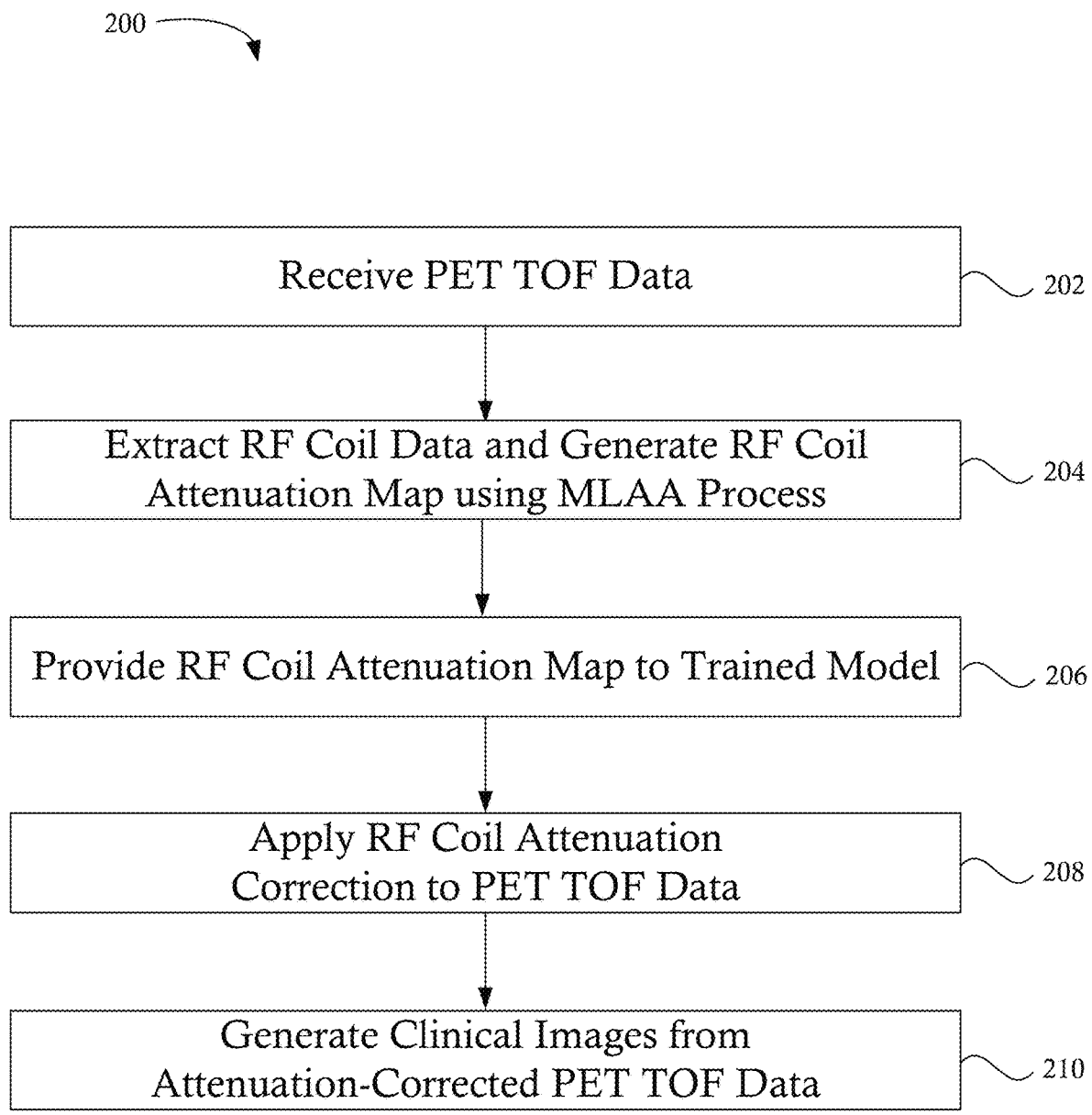
FIG. 3 is a flowchart illustrating a method of attenuation correction using RF data and a maximum likelihood estimation of activity and attenuation process, in accordance with some embodiments.
Figure 4:
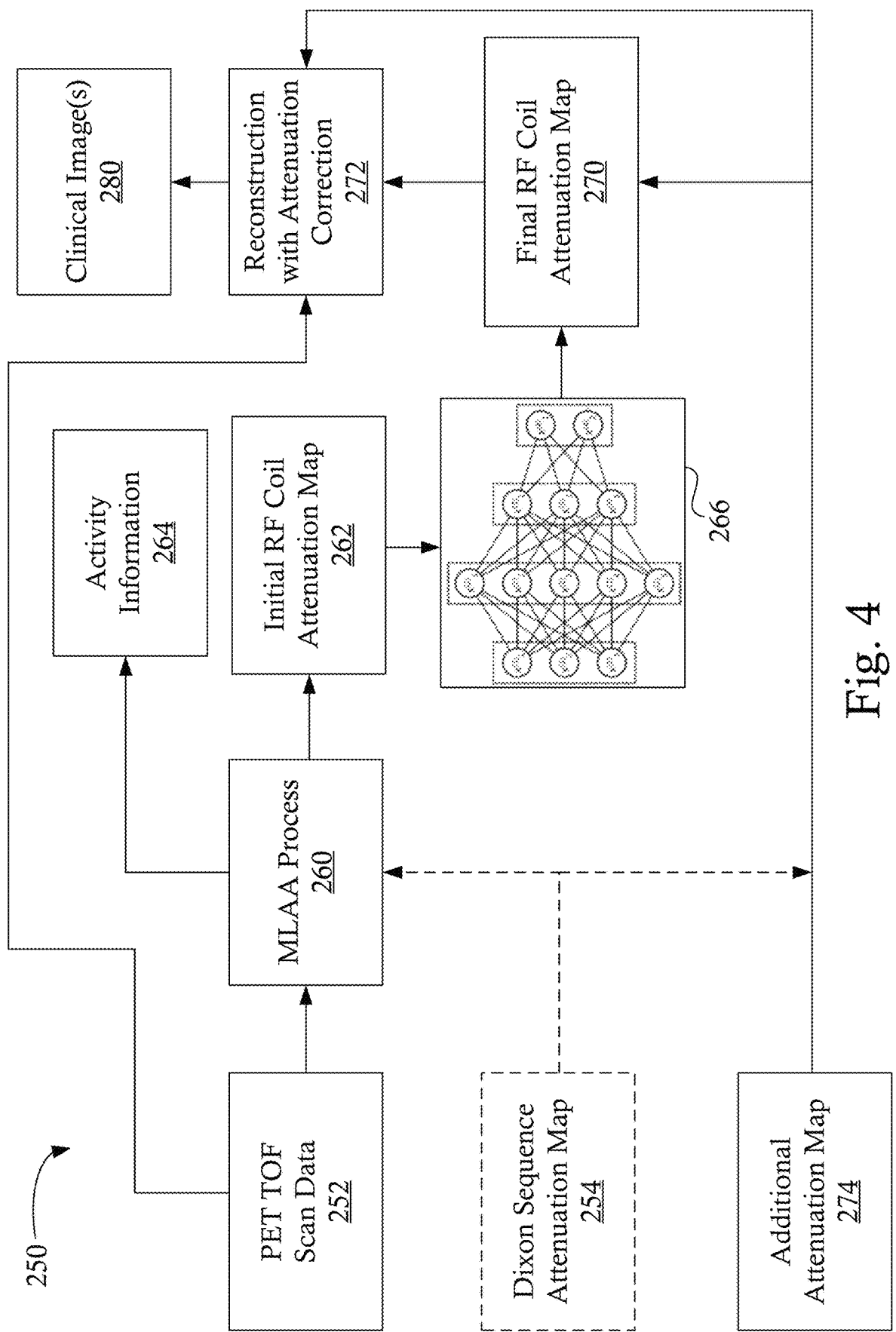
FIG. 4 is a process flow for performing attenuation correction using RF data and a maximum likelihood estimation of activity and attenuation process, according to the method illustrated in FIG. 3, in accordance with some embodiments.

FIG. 3 is a flowchart 200 illustrating a method of attenuation correction including RF coil attenuation correction, in accordance with some embodiments. FIG. 4 is a process flow 250 for performing attenuation correction including RF coil attenuation correction according to the method illustrated in FIG. 3, in accordance with some embodiments. At step 202, a set of PET TOF data 252 is received. The set of PET TOF data 252 is generated by a PET imaging modality collocated with an MR imaging modality and therefore includes attenuation caused by collocated RF coils. Although specific embodiments are discussed herein, it will be appreciated that the disclosed systems and methods can be applied to any scan data and/or scan modalities including collocated RF coils resulting in attenuation in the data. In some embodiments, the PET TOF data includes a known emission source (e.g., phantom) positioned adjacent to a patient during acquisition of the PET TOF data.

At step 204, RF coil attenuation factors are estimated and an initial RF coil attenuation map 262 is generated from the PET TOF data 252 using a maximum likelihood estimation of activity and attenuation (MLAA) process 260. The initial RF coil attenuation map 262 will have a poor signal-to-noise ratio (SNR). In some embodiments, an attenuation map generated from a Dixon sequence can be provided to the MLAA process 260. The Dixon Sequence attenuation map 254 can be generated from MR imaging data obtained from a collocated MR imaging modality, such as the second imaging modality 14.

At step 206, the initial RF-coil attenuation map 262 is provided to a trained attenuation model 266 configured to refine the initial RF-coil attenuation map 262 to generate a final RF-coil attenuation map 270 suitable for use in attenuation correction of a data set, such as the PET TOF data. The trained model 266 includes a machine learning model trained using a training data set, as discussed in greater detail below. In some embodiments, the trained attenuation model 266 includes a neural network. The trained attenuation model 266 generates a final RF-coil attenuation map 270. The final RF-coil attenuation map 262 is configured to correct for attenuation caused by the RF coils during acquisition of scan data, such as during acquisition of the PET TOF data 252. As discussed in greater detail below, the trained attenuation model 266 can be trained using PET TOF data obtained during scans of known emission sources (e.g., phantoms) and/or based on PET TOF data registered to predetermined attenuation maps, such as CT-based attenuation maps.

At step 208, an attenuation correction process 272 is applied to the PET TOF data 252. Attenuation correction is applied using the final RF-based attenuation map 270 and additional attenuation factors or maps. In some embodiments, one or more additional attenuation maps 274, such as a traditional PET attenuation maps, are used for additional attenuation correction of the first set of scan data 252. In some embodiments, the final RF-based attenuation map and the additional attenuation map 274 are combined into a single attenuation map, which is provided to the attenuation correction process 272, although it will be appreciated that multiple independent attenuation maps can be received.

At step 210, one or more clinical images 280 are reconstructed from the attenuation-corrected PET TOF data. The clinical images 280 can include, for example, diagnostic images, planning images, and/or any other suitable clinical images. The images can be stored on a non-transitory medium and/or provided to a clinician for use in diagnostics, planning, and/or other purposes. The one or more clinical images 280 can be stored as image files, as attenuation-corrected data, and/or using any other suitable storage method.

The method of attenuation correction for RF coil attenuation discussed in conjunction with FIG. 3 provides distinct advantages to PET/MR systems. For example, current imaging systems primarily rely on CT scans for generation of attenuation maps, which accounts for patient-specific attenuation. However, PET/MR systems do not include a CT component. The use of RF coil attenuation correction maps allows for correction of previously unaddressed attenuation in PET/MR systems, providing more accurate clinical images, fewer false positive/negatives, and improving diagnostic and clinical outcomes. For example, by performing RF coil attenuation, the disclosed systems and methods avoid activity underestimation errors.

Figure 5:
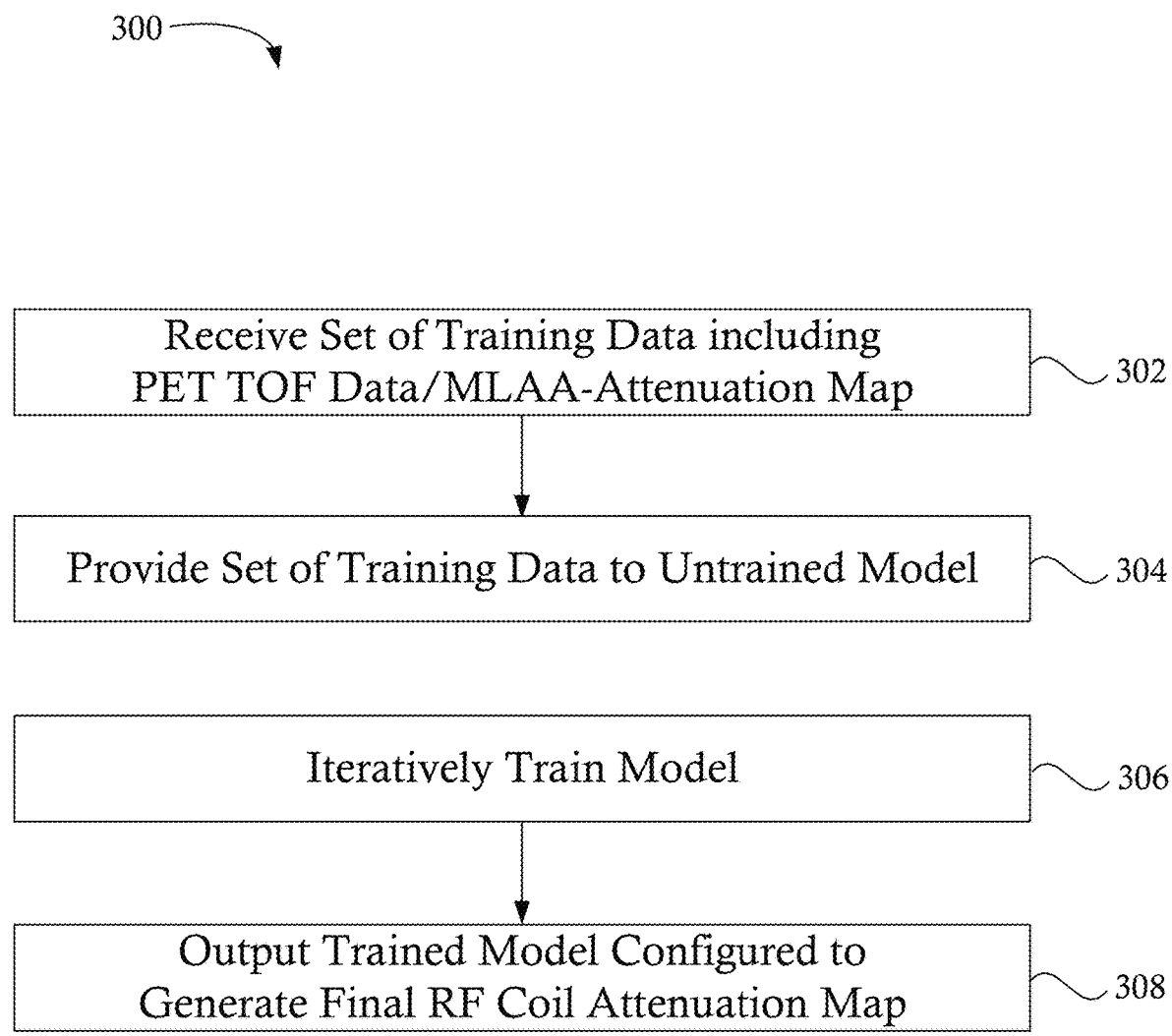
FIG. 5 is a flowchart illustrating a method of training a machine learning function for use in the method of attenuation correction illustrated in FIG. 3, in accordance with some embodiments.
Figure 6:
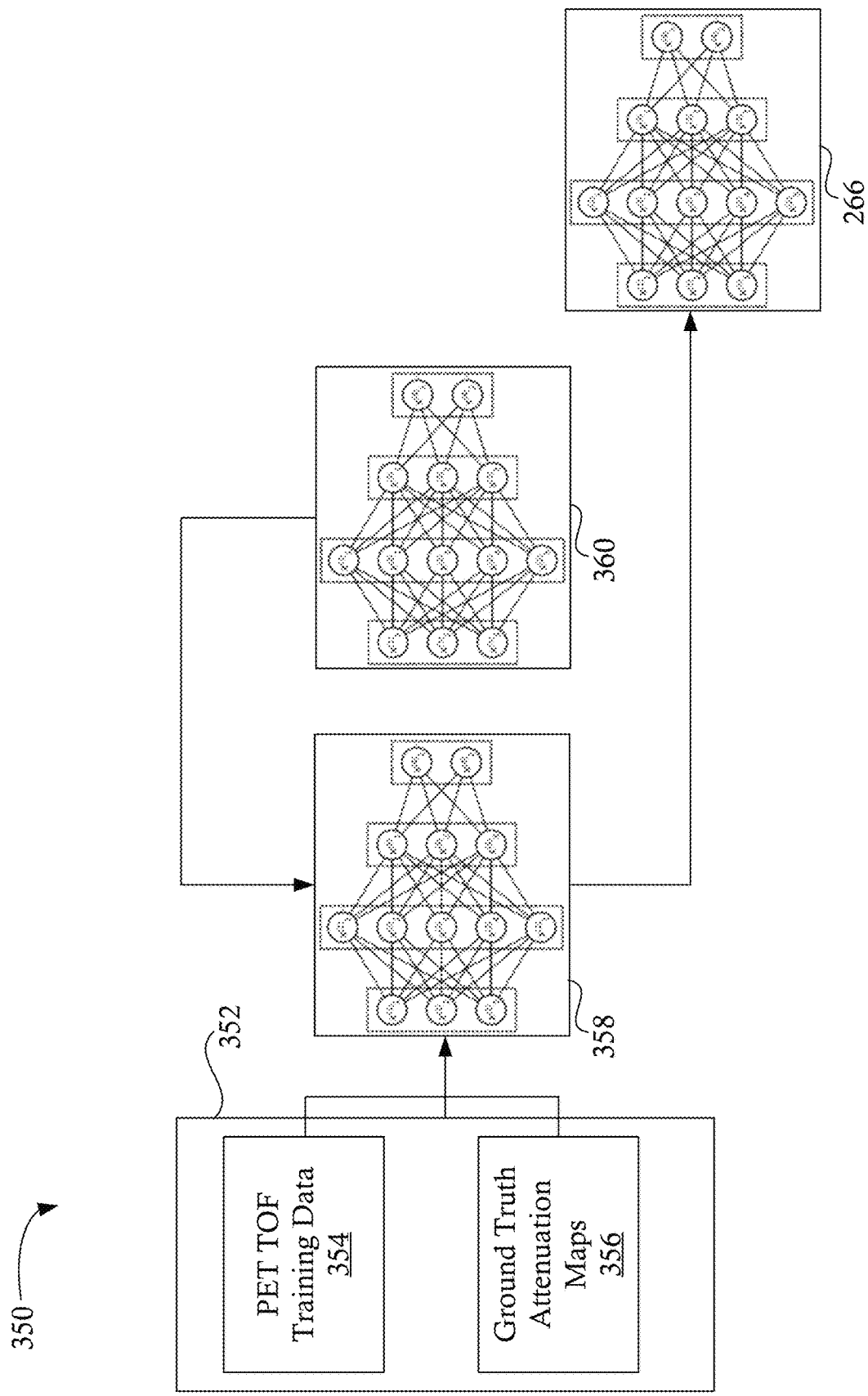
FIG. 6 is a process flow for training a machine learning function according to the method illustrated in FIG. 5, in accordance with some embodiments.

FIG. 5 is a flowchart 300 illustrating a method of training a machine learning model, in accordance with some embodiments. FIG. 6 is a process flow 350 for training a machine learning model according to the method illustrated in FIG. 4, in accordance with some embodiments. At step 302, a set of training data 352 is received. The set of training data includes labeled data configured to iteratively train an untrained machine learning model 358 to generate an attenuation correction map. The set of training data 352 includes a set of PET TOF data 354 and a set of associated attenuation maps 356. The set of attenuation maps 356 can be generated based on scans of a known emission source (e.g., phantom) using the same imaging modality configured to generate the set of PET TOF data and/or a separate imaging modality. In some embodiments, the set of attenuation maps 356 include attenuation maps generated by a separate imaging modality, such as a CT imaging modality, registered to the PET TOF data, The set of training data 352 can include MLAA-generated RF coil attenuation maps, CT registered attenuation maps, Dixon sequence attenuation maps, and/or any other suitable attenuation maps for each subset of PET TOF data in the set of PET TOF data 354. In some embodiments, the training set may omit the PET TOF data and only include the associated (i.e., ground truth) attenuation maps and MLAA-generated attenuation maps. In some embodiments, the untrained model 358 is configured to apply an MLAA process to generate an initial RF coil attenuation map from a subset of the PET TOF data 354 and further trained to apply process to increase the SNR of the initial RF coil attenuation map based on one or more additional attenuation maps, such as a CT registered attenuation map and/or ground truth attenuation map.

At step 304, the set of training data 352 is provided to the untrained machine learning model 358 and, at step 306, the untrained machine learning model performs an iterative training process. In some embodiments, the iterative training process includes training a first set of embedding (or hidden) layers to refine an initial RF coil attenuation map. The refined RF coil attenuation map is compared to one or more associated attenuation maps in the set of associated attenuation maps 356 and adjustments are made to the untrained machine learning model 358. In some embodiments, the machine learning model 358 is iteratively trained to refine the MLAA-generated RF coil attenuation map to increase the SNR. An intermediate machine learning model 360 is generated and is used in subsequent iterative training steps. The intermediate machine learning model 360 is further refined using the set of training data 352 to generate a trained machine learning model 266. As discussed above, in some embodiments, training the untrained machine learning model can include training a second set of embedding layers to generate an initial RF coil attenuation map from a subset of the PET TOF data. In such embodiments, the initial RF coil attenuation map can be generated prior to applying the first set of embedding layers to refine the SNR of the initial RF coil attenuation map. Although embodiments are discussed herein including an untrained machine learning model 358, it will be appreciated that a previously trained machine learning model can be used as an initial learning model 358 for use in the iterative training process.

At step 308, the trained machine learning model 266 is output. The trained machine learning model 266 is configured to generate a final RF coil attenuation map for use in attenuation correction of PET TOF data. The trained machine learning model 266 can be used to generate RF coil attenuation maps for attenuation correction of PET TOF data according to the methods discussed herein, for example, as discussed in conjunction with FIG. 3.

A first embodiment includes a computer-implemented method. The method includes the steps of receiving PET time-of-flight (TOF) data generated by a PET imaging modality collocated with an MR imaging modality, generating an initial RF coil attenuation, applying a trained model configured to improve a signal to noise ratio of the initial RF coil attenuation map to generate a final RF coil attenuation map, performing attenuation correction of the PET TOF data based on the final RF coil attenuation map, and generating an image from attenuation corrected PET TOF data.

In the first embodiment, the initial RF coil attenuation map can be generated by a maximum likelihood estimation of activity and attenuation (MLAA) process. The MLAA can estimate one or more RF coil attenuation factors.

In the first embodiment, the MLAA process can receive a Dixon sequence attenuation map generated from MR data generated by the collocated MR imaging modality. The initial RF coil attenuation map is generated at least in part based on the Dixon sequence attenuation map.

In the first embodiment, attenuation correction of the PET TOF data can be performed based on a second attenuation map generated by a CT imaging modality separate from the PET imaging modality and the MR imaging modality.

In the first embodiment, the trained model can be trained based on PET TOF data obtained from a known emission source and/or based on PET TOF data registered to a CT-based mu map.

In a second embodiment, a system includes a PET imaging modality configured to generate PET TOF data, a MR imaging modality collocated with the PET imaging modality including a plurality of RF coils, a non-transitory memory having instructions stored thereon, and a processor configured to read the instructions to: receive the PET TOF data, generate an initial RF coil attenuation map from the RF coil attenuation data, apply a trained model configured to improve a signal to noise ratio of the initial RF coil attenuation map to generate a final RF coil attenuation map, perform attenuation correction of the PET TOF data based in part on the final RF coil attenuation map, and reconstruct an image from attenuation corrected PET TOF data.

In the second embodiment, the initial RF coil attenuation map can be generated by a maximum likelihood estimation of activity and attenuation (MLAA) process. The MLAA process can estimate one or more RF coil attenuation factors.

In the second embodiment, the processor is configured to read the instructions to generate a Dixon sequence attenuation map from MR data generated by the MR imaging modality. The Dixon sequence attenuation map is provided to the MLAA process and the initial RF coil attenuation map is generated at least in part based on the Dixon sequence attenuation map.

In the second embodiment, the processor is configured to read the instructions to perform attenuation correction of the PET TOF data based on a second attenuation map generated by a CT imaging modality separate from the PET imaging modality and the MR imaging modality.

In the second embodiment, the trained model is trained based on PET TOF data obtained from a known emission source and/or PET TOF data registered to a CT-based mu map.

In a third embodiment, a computer-implemented method of training a model for generating a RF coil attenuation map includes receiving a set of training data comprising one or more subsets of PET TOF data and one or more ground truth attenuation maps, iteratively training an untrained model based on the set of training data, and outputting a trained model configured to increase a signal to noise ratio of an initial RF coil attenuation map to generate a final RF coil attenuation map. Each of the one or more ground truth attenuation maps is associated with one of the one or more subsets of PET TOF data.

In the third embodiment, each of the subsets of PET TOF data can include a maximum likelihood estimation of activity and attenuation (MLAA) generated attenuation map.

In the third embodiment, the computer-implemented method can include a step of generating the initial RF coil attenuation map using an maximum likelihood estimation of activity and attenuation (MLAA) process.

In the third embodiment, each of the one or more ground truth attenuation maps are generated from PET TOF data generated using a known emission source and/or based on computerized tomography (CT) scan data.

In the third embodiment, the one or more ground truth attenuation maps can include a Dixon sequence attenuation map In a fourth embodiment, the trained model used in either of the first or second embodiments can be generated by the computer-implemented method of the third embodiment.

In a fifth embodiment, a non-transitory computer-readable medium includes instructions, which, when executed by a processor, cause the processor to carry out the method of the first, third, or fourth embodiments.

What is claimed is:

1. A computer-implemented method for attenuation correction, comprising:
    receiving, by at least one processor, positron emission tomography (PET) time-of-flight (TOF) data generated by a PET imaging modality collocated with a magnetic resonance (MR) imaging modality;
    extracting, by the at least one processor, Radio Frequency (RF) coil attenuation data from the PET TOF data, the RF coil attenuation data characterizing an attenuation caused by collocated RF coils of the MR imaging modality;
    generating, by the at least one processor, an initial Radio Frequency (RF) coil attenuation map based on the RF coil attenuation data;
    applying, by the at least one processor, a trained model configured to improve a signal to noise ratio of the initial RF coil attenuation map to generate a final RF coil attenuation map, the final RF coil attenuation map having a higher signal to noise ratio than the initial RF coil attenuation map and configured to correct for the attenuation caused by the RF coils during acquisition of the PET TOF data, wherein the trained model is generated based on training an untrained model using an iterative training process that comprises:
        training a first set of embedding layers of an untrained model based on a set of training data to generate a first RF coil attenuation map; and
        subsequent to training the first set of embedding layers, training a second set of embedding layers of the untrained model based on the set of training data and the first RF coil attenuation map generated by the first set of embedding layers, wherein the training of the second set of embedding layers causes a refinement of the first RF coil attenuation map, the training comprising comparing the refined first RF coil attenuation map to one or more ground truth attenuation maps and adjusting at least one of the second set of embedding layers of the untrained model based on the comparison after each iteration;
    performing, by the at least one processor, attenuation correction of the PET TOF data based in part on the final RF coil attenuation map; and
    reconstructing, by the at least one processor, an image from the attenuation corrected PET TOF data wherein each of the one or more ground truth attenuation maps are generated from PET TOF data generated using a known emission source.

2. The computer-implemented method of claim 1, wherein the initial RF coil attenuation map is generated by a maximum likelihood estimation of activity and attenuation (MLAA) process.

3. The computer-implemented method of claim 2, wherein the MLAA process estimates one or more RF coil attenuation factors.

4. The computer-implemented method of claim 2, wherein the MLAA process receives a Dixon sequence attenuation map generated from MR data generated by the collocated MR imaging modality, and wherein the initial RF coil attenuation map is generated at least in part based on the Dixon sequence attenuation map.

5. The computer-implemented method of claim 1, comprising performing the attenuation correction of the PET TOF data based on a second attenuation map generated by a Computed Tomography (CT) imaging modality separate from the PET imaging modality and the MR imaging modality.

6. The computer-implemented method of claim 1, wherein the trained model is trained based on PET TOF data obtained from a known emission source.

7. The computer-implemented method of claim 1, wherein the trained model is trained based on PET TOF data registered to a CT-based mu map.

8. A system, comprising:
    a PET imaging modality configured to generate positron emission tomography (PET) time-of-flight (TOF) data;
    a MR imaging modality collocated with the PET imaging modality, comprising a plurality of Radio Frequency (RF) coils; and
    a non-transitory memory having instructions stored thereon and a processor configured to read the instructions to:
        receive the PET TOF data;
        extract Radio Frequency (RF) coil attenuation data from the PET TOF data, the RF coil attenuation data characterizing an attenuation caused by collocated RF coils of the MR imaging modality;
        generate an initial RF coil attenuation map based on the RF coil attenuation data;
        apply a trained model configured to improve a signal to noise ratio of the initial RF coil attenuation map to generate a final RF coil attenuation map, the final RF coil attenuation map having a higher signal to noise ratio than the initial RF coil attenuation map and configured to correct for the attenuation caused by the RF coils during acquisition of the PET TOF data, wherein the trained model is generated based on training an untrained model using an iterative training process that comprises:
            training a first set of embedding layers of an untrained model based on a set of training data to generate a first RF coil attenuation map; and
            subsequent to training the first set of embedding layers, training a second set of embedding layers of the untrained model based on the set of training data and the first RF coil attenuation map generated by the first set of embedding layers, wherein the training of the second set of embedding layers causes a refinement of the first RF coil attenuation map, the training comprising comparing the refined first RF coil attenuation map to one or more ground truth attenuation maps and adjusting at least one of the second set of embedding layers of the untrained model based on the comparison after each iteration;

perform attenuation correction of the PET TOF data based in part on the final RF coil attenuation map; and reconstruct an image from the attenuation corrected PET TOF data wherein each of the one or more ground truth attenuation maps are generated from PET TOF data generated using a known emission source.

9. The system of claim 8, wherein the initial RF coil attenuation map is generated by a maximum likelihood estimation of activity and attenuation (MLAA) process.

10. The system of claim 9, wherein the MLAA process estimates one or more RF coil attenuation factors.

11. The system of claim 9, wherein the processor is configured to read the instructions to generate a Dixon sequence attenuation map from MR data generated by the MR imaging modality, wherein the Dixon sequence attenuation map is provided to the MLAA process and the initial RF coil attenuation map is generated at least in part based on the Dixon sequence attenuation map.

12. The system of claim 8, wherein the processor is configured to read the instructions to perform the attenuation correction of the PET TOF data based on a second attenuation map generated by a CT imaging modality separate from the PET imaging modality and the MR imaging modality.

13. The system of claim 8, wherein the trained model is trained based on PET TOF data obtained from a known emission source.

14. The system of claim 8, wherein the trained model is trained based on PET TOF data registered to a CT-based mu map.

15. A computer-implemented method of training a model for generating a Radio Frequency (RF) coil attenuation map, the method performed by at least one processor configured to read instructions stored in a non-transitory memory and perform the method, the method comprising:

receiving, by the at least one processor, a set of training data comprising one or more subsets of positron emission tomography (PET) time-of-flight (TOF) data and one or more ground truth attenuation maps, wherein each of the one or more ground truth attenuation maps is associated with one of the one or more subsets of PET TOF data;

iteratively training, by the at least one processor, an untrained model, the iterative training comprising:

training, by the at least one processor, a first set of embedding layers of the untrained model based on the set of training data to generate an initial RF coil attenuation map;

subsequent to training the first set of embedding layers, training, by the at least one processor, a second set of embedding layers of the untrained model based on the set of training data and the first RF coil attenuation map generated by the first set of embedding layers, wherein the training of the second set of embedding layers causes a refinement of the initial RF coil attenuation map, the training comprising comparing the initial RF coil attenuation map to the one or more ground truth attenuation maps and adjusting at least one of the second set of embedding layers of the untrained model based on the comparison after each iteration; and based on the training, outputting, by the at least one processor, a trained model configured to increase a signal to noise ratio of the initial RF coil attenuation map to generate a final RF coil attenuation map wherein each of the one or more ground truth attenuation maps are generated from PET TOF data generated using a known emission source.

16. The computer-implemented method of claim 15, wherein each of the subsets of PET TOF data comprise a maximum likelihood estimation of activity and attenuation (MLAA) generated attenuation map.

17. The computer-implemented method of claim 15, comprising generating the initial RF coil attenuation map using an maximum likelihood estimation of activity and attenuation (MLAA) process.

18. The computer-implemented method of claim 15, wherein each of the one or more ground truth attenuation maps are generated based on computed tomography (CT) scan data.

19. The computer-implemented method of claim 15, wherein the one or more ground truth attenuation maps include a Dixon sequence attenuation map.

* * * * *